(12) United States Patent
Liu

(10) Patent No.: US 11,147,933 B2
(45) Date of Patent: Oct. 19, 2021

(54) ELECTRONIC CIGARETTE

(71) Applicant: Tuanfang Liu, Shenzhen (CN)

(72) Inventor: Tuanfang Liu, Shenzhen (CN)

( * ) Notice: Subject to any disclaimer, the term of this patent is extended or adjusted under 35 U.S.C. 154(b) by 220 days.

(21) Appl. No.: 16/697,141

(22) Filed: Nov. 26, 2019

(65) Prior Publication Data

US 2020/0404980 A1 Dec. 31, 2020

(30) Foreign Application Priority Data

Jun. 29, 2019 (CN) .......................... 201910580782.3
Jun. 29, 2019 (CN) .......................... 201921014313.7

(51) Int. Cl.
*A24F 13/00* (2006.01)
*A24F 17/00* (2006.01)
*A24F 25/00* (2006.01)
*A61M 11/04* (2006.01)

(52) U.S. Cl.
CPC ... *A61M 11/042* (2014.02); *A61M 2205/8206* (2013.01)

(58) Field of Classification Search
CPC ....... A24F 40/10; A24F 40/40; A61M 11/042; A61M 2205/8206
See application file for complete search history.

(56) References Cited

U.S. PATENT DOCUMENTS

| 2017/0000190 | A1* | 1/2017 | Wu | ........................ | A24F 40/485 |
| 2020/0054074 | A1* | 2/2020 | Xiaojun | ..................... | A24F 9/16 |
| 2020/0337383 | A1* | 10/2020 | Nguyen | .................. | A24F 40/53 |

* cited by examiner

*Primary Examiner* — Abdullah A Riyami
*Assistant Examiner* — Thang H Nguyen
(74) *Attorney, Agent, or Firm* — Matthias Scholl P.C.; Matthias Scholl

(57) ABSTRACT

An electronic cigarette, including: an atomization assembly and a battery assembly. The atomization assembly is disposed on the battery assembly. The atomization assembly includes a top cap; a buckle; a first fixing part; a first magnet; a steel tube; a second fixing part; a mouthpiece; an observation tube; a vapor tube; an e-liquid container; an e-liquid guide; a threaded joint; a fixing ring fixing the threaded joint; a second magnet; a heating unit; a first silica gel; a fixed seat; a first insulation ring; and a joint. The battery assembly includes an elastic electrode; a third magnet; a second insulation ring; a copper ring; a cartridge; a battery; a second silica gel; a pneumatic switch; a control plate; a base; and a bottom cap. The top cap includes a cavity and the first magnet is disposed in the cavity of the top cap.

1 Claim, 5 Drawing Sheets

ELECTRONIC CIGARETTE

CROSS-REFERENCE TO RELAYED APPLICATIONS

Pursuant to 35 U.S.C. § 119 and the Paris Convention Treaty, this application claims foreign priority to Chinese Patent Application No. 201910580782.3 filed Jun. 29, 2019 and to Chinese Patent Application No. 201921014313.7 filed Jun. 29, 2019. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to an electronic cigarette.

Electronic cigarettes atomize nicotine-containing e-liquid.

Conventional electronic cigarettes include a fixed e-liquid container. The recharge of the e-liquid is troublesome.

SUMMARY

The disclosure provides an electronic cigarette comprising a detachable e-liquid container.

An electronic cigarette comprises an atomization assembly and a battery assembly. The atomization assembly is disposed on the battery assembly.

The atomization assembly comprises a top cap; a buckle; a first fixing part; a first magnet; a steel tube; a second fixing part; a mouthpiece; an observation tube; a vapor tube; an e-liquid container; an e-liquid guide; a threaded joint; a fixing ring fixing the threaded joint; a second magnet; a heating unit; a first silica gel; a fixed seat; a first insulation ring; and a joint.

The battery assembly comprises an elastic electrode; a third magnet; a second insulation ring; a copper ring; a cartridge; a battery; a second silica gel; a pneumatic switch; a control plate; a base; and a bottom cap.

The top cap comprises a cavity and the first magnet is disposed in the cavity of the top cap; the buckle is disposed between the top cap and the first fixing part; the top cap is disposed on the first fixing part; the first fixing part and the second fixing part are disposed on two ends of the steel tube, respectively.

The mouthpiece is disposed on the observation tube; the vapor tube is disposed in the observation tube; the fixing ring is fixed on the observation tube; the second magnet is directly connected to the threaded joint.

The first silica gel is sheathed on the heating unit; the heating unit is fixed on the fixed seat; the first insulation ring is sheathed on the joint, and the joint is disposed in the fixed seat; the fixed seat is in threaded connection to the threaded joint; one end of the e-liquid guide is disposed on the heating unit; the other end of the e-liquid guide comprises a tip extending into the e-liquid container; the e-liquid guide and the e-liquid container are disposed in the observation tube; and the steel tube is sheathed on the mouthpiece; the elastic electrode and the second insulation ring are disposed in the copper ring; the third magnet is disposed on the copper ring; the copper ring is disposed on the cartridge.

The pneumatic switch is disposed on the control plate; the control plate is attached to the battery; the second silica gel is sheathed on the pneumatic switch; the control plate is disposed on the base; the battery, the control plate and the base are disposed in the cartridge; and the bottom cap is attached to one end of the cartridge to limit the base in the cartridge.

DETAILED DESCRIPTION

To further illustrate, embodiments detailing an electronic cigarette are described below. It should be noted that the following embodiments are intended to describe and not to limit the disclosure.

Figure 1:
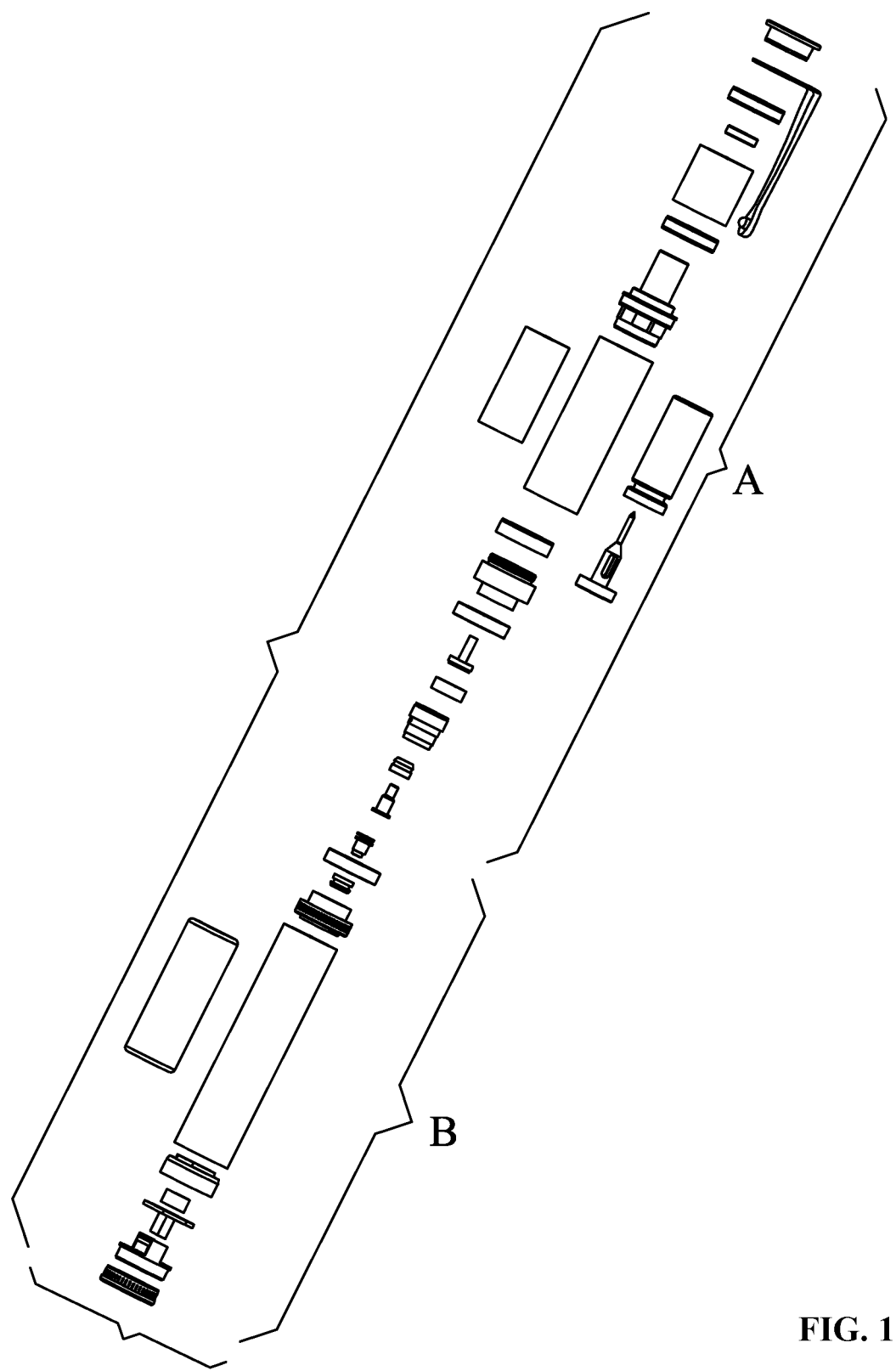
FIG. 1 is an exploded view of an electronic cigarette according to one embodiment of the disclosure.
Figure 2:
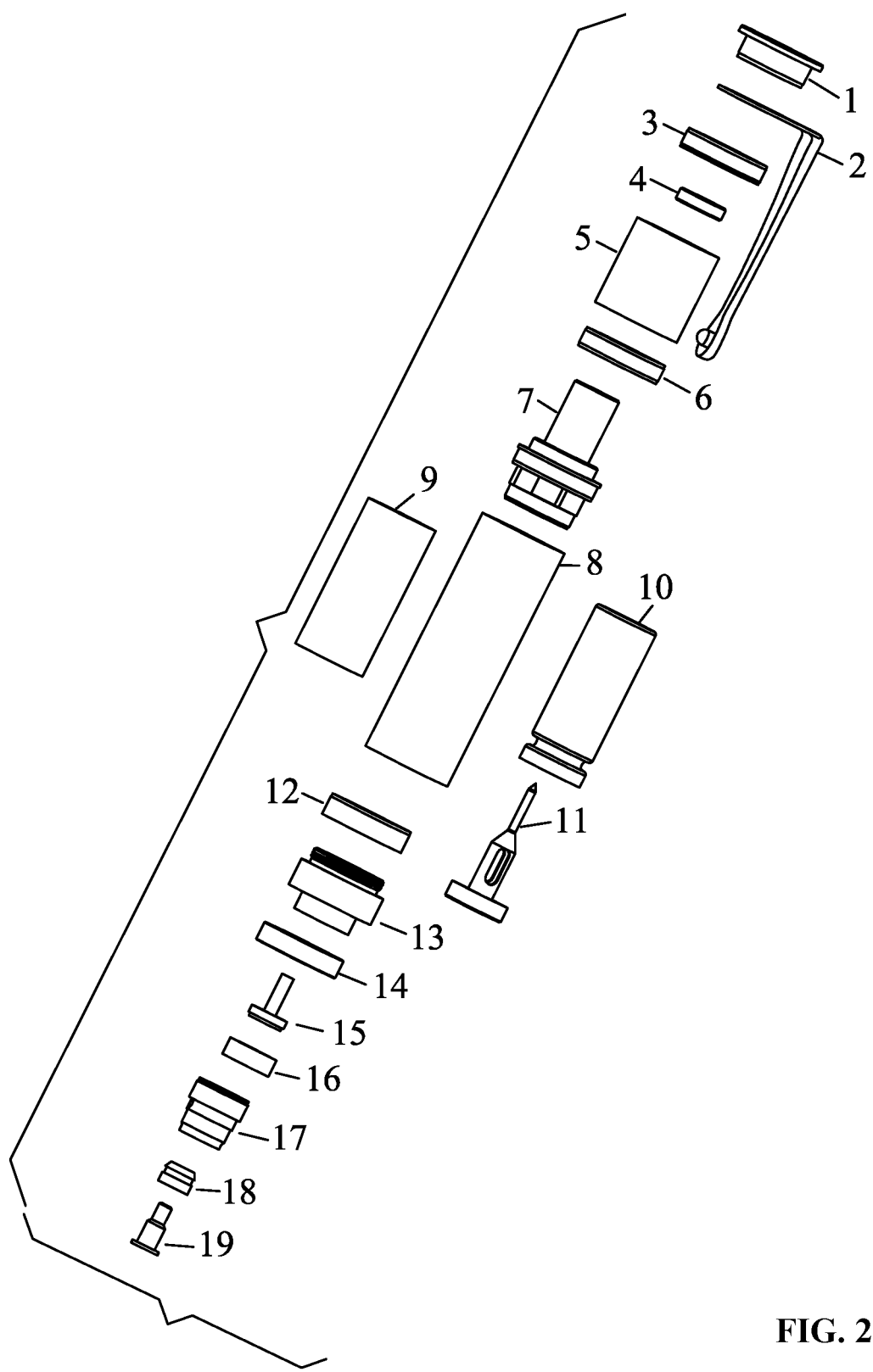
FIG. 2 is an exploded view of an atomization assembly of an electronic cigarette according to one embodiment of the disclosure.
Figure 3:
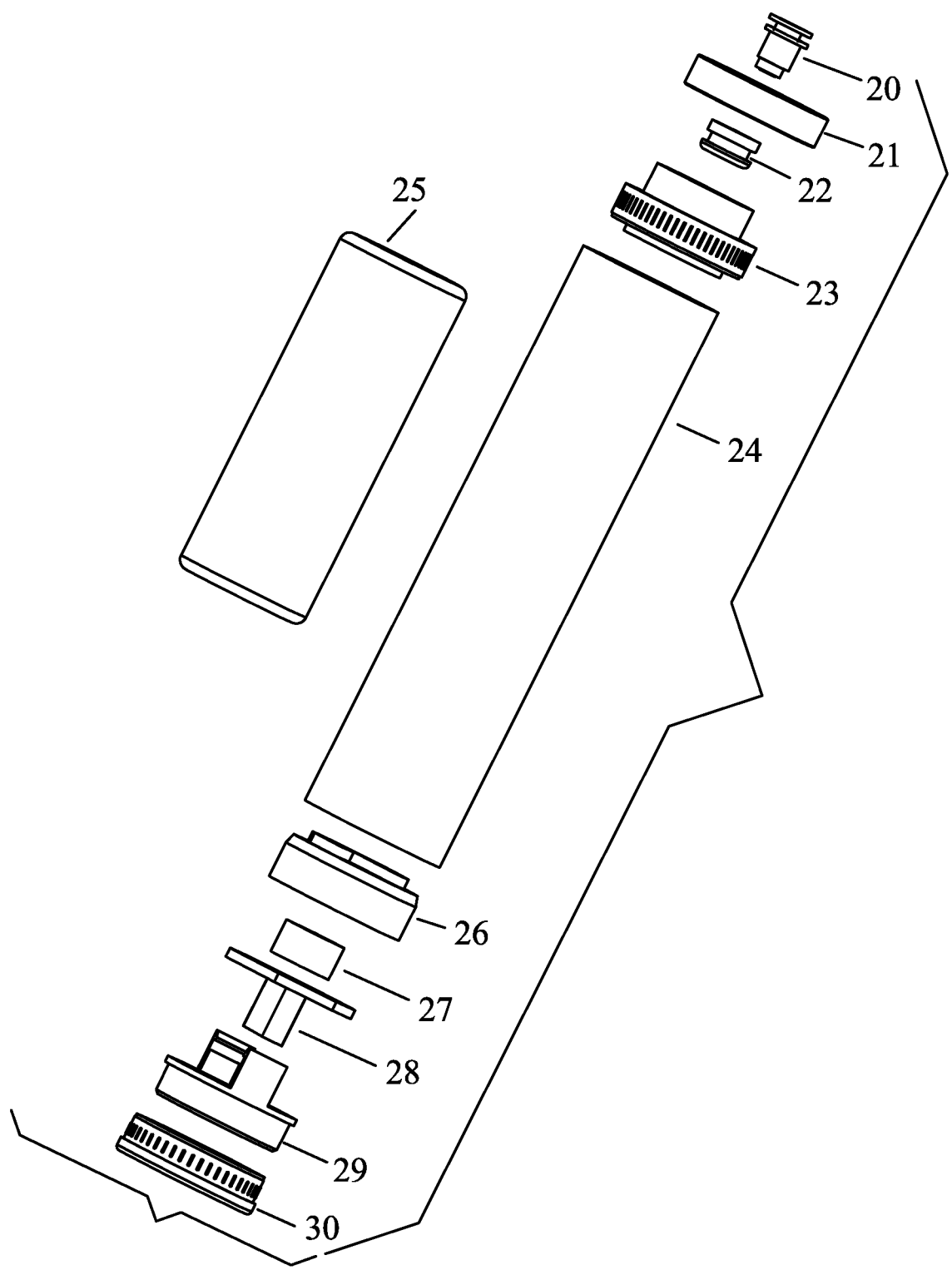
FIG. 3 is an exploded view of a battery assembly of an electronic cigarette according to one embodiment of the disclosure.
Figure 4:
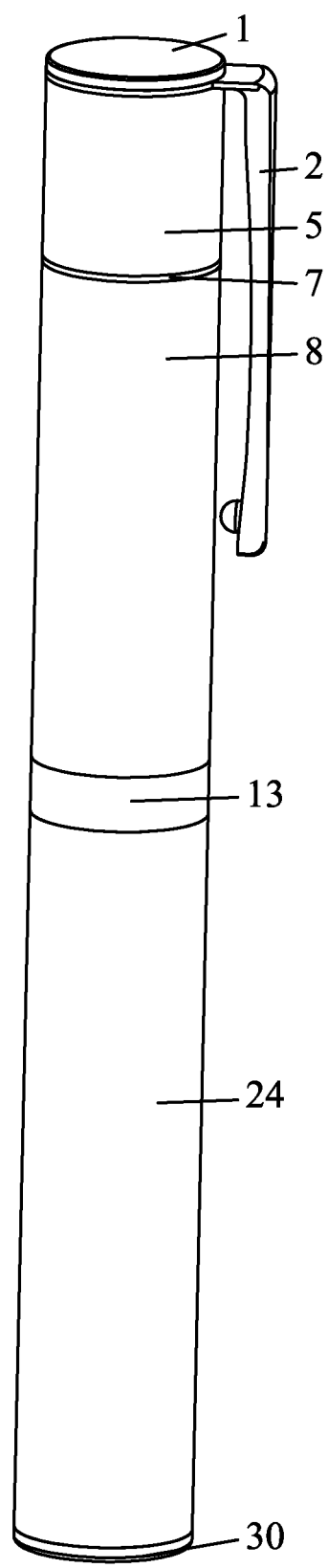
FIG. 4 is a stereogram of an electronic cigarette according to one embodiment of the disclosure.
Figure 5:
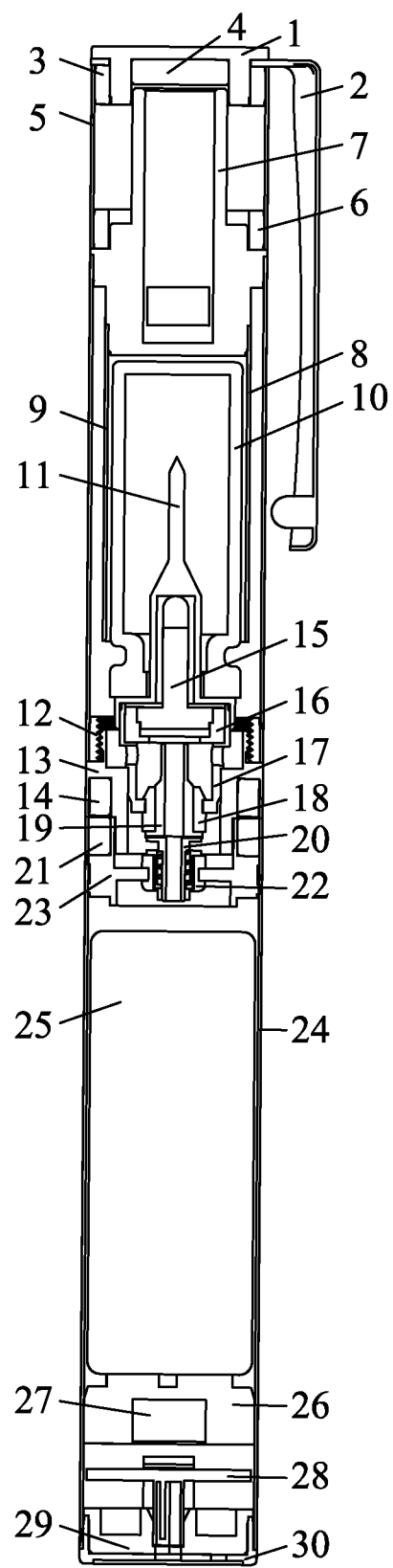
FIG. 5 is a sectional view of an electronic cigarette according to one embodiment of the disclosure.

As shown in FIGS. 1-5, an electronic cigarette comprises an atomization assembly A and a battery assembly B. The atomization assembly A is disposed on the battery assembly B. The atomization assembly A comprises a top cap 1; a buckle 2; a first fixing part 3; a first magnet 4; a steel tube 5; a second fixing part 6; a mouthpiece 7; an observation tube 8; a vapor tube 9; an e-liquid container 10; an e-liquid guide 11; a threaded joint 13; a fixing ring 12 fixing the threaded joint 13; a second magnet 14; a heating unit 15; a first silica gel 16; a fixed seat 17; a first insulation ring 18; and a joint 19. The battery assembly B comprises an elastic electrode 20; a third magnet 21; a second insulation ring 22; a copper ring 23; a cartridge 24; a battery 25; a second silica gel 26; a pneumatic switch 27; a control plate 28; a base 29; and a bottom cap 30.

The top cap 1 comprises a cavity and the first magnet 4 is disposed in the cavity of the top cap 1; the buckle 2 is disposed between the top cap 1 and the first fixing part 3; the top cap 1 is disposed on the first fixing part 3; the first fixing part 3 and the second fixing part 6 are disposed on two ends of the steel tube 5, respectively; the mouthpiece 7 is disposed on the observation tube 8; the vapor tube 9 is disposed in the observation tube 8; the fixing ring 12 is fixed on the observation tube 8; the second magnet 14 is directly connected to the threaded joint 13; the first silica gel 16 is sheathed on the heating unit 15; the heating unit 15 is fixed on the fixed seat 17; the first insulation ring 18 is sheathed on the joint 19, and the joint 19 is disposed in the fixed seat 17; the fixed seat 17 is in threaded connection to the threaded joint 13; one end of the e-liquid guide 11 is disposed on the heating unit 15; the other end of the e-liquid guide 11 comprises a tip extending into the e-liquid container 10; the e-liquid guide 11 and the e-liquid container 10 are disposed in the observation tube 8; and the steel tube 5 is sheathed on the mouthpiece 7; the elastic electrode 20 and the second insulation ring 22 are disposed in the copper ring 23; the third magnet 21 is disposed on the copper ring 23; the copper ring 23 is disposed on the cartridge 24; the pneumatic switch 27 is disposed on the control plate 28; the control plate 28 is attached to the battery 25; the second silica gel 26 is sheathed on the pneumatic switch 27; the control plate 28 is disposed on the base 29; the battery 25, the control plate 28 and the base are disposed in the cartridge 24; and the bottom cap 30 is attached to one end of the cartridge to limit the base 29 in the cartridge.

The e-liquid container 10 has a scale, the top part thereof toward the mouthpiece is sealed by silica gel and aluminum foil. In use, the e-liquid container 10 is inserted onto the e-liquid guide 11, so that the e-liquid can penetrate into the heating unit 15 via the opening of the e-liquid guide 11. This simplifies the operation of charging e-liquid.

The atomization assembly and the battery assembly are connected to each other via the second magnet 14 and the third magnet 21. The entire electronic cigarette is in the shape of a pen having a buckle, so it is easy to carry.

It will be obvious to those skilled in the art that changes and modifications may be made, and therefore, the aim in the appended claims is to cover all such changes and modifications.

What is claimed is:

1. A device, comprising: an atomization assembly and a battery assembly; the atomization assembly comprising:
   1) a top cap;
   2) a buckle;
   3) a first fixing part;
   4) a first magnet;
   5) a steel tube;
   6) a second fixing part;
   7) a mouthpiece;
   8) an observation tube;
   9) a vapor tube;
   10) an e-liquid container;
   11) an e-liquid guide;
   12) a threaded joint;
   13) a fixing ring fixing the threaded joint;
   14) a second magnet;
   15) a heating unit;
   16) a first silica gel;
   17) a fixed seat;
   18) a first insulation ring; and
   19) a joint;

the battery assembly comprising:
   20) an elastic electrode;
   21) a third magnet;
   22) a second insulation ring;
   23) a copper ring;
   24) a cartridge;
   25) a battery;
   26) a second silica gel;
   27) a pneumatic switch;
   28) a control plate;
   29) a base; and
   30) a bottom cap;

wherein:
   the top cap comprises a cavity and the first magnet is disposed in the cavity of the top cap; the buckle is disposed between the top cap and the first fixing part; the top cap is disposed on the first fixing part; the first fixing part and the second fixing part are disposed on two ends of the steel tube, respectively;

the mouthpiece is disposed on the observation tube; the vapor tube is disposed in the observation tube; the fixing ring is fixed on the observation tube; the second magnet is directly connected to the threaded joint;

the first silica gel is sheathed on the heating unit; the heating unit is fixed on the fixed seat; the first insulation ring is sheathed on the joint, and the joint is disposed in the fixed seat; the fixed seat is in threaded connection to the threaded joint;

one end of the e-liquid guide is disposed on the heating unit; the other end of the e-liquid guide comprises a tip extending into the e-liquid container; the e-liquid guide and the e-liquid container are disposed in the observation tube; and the steel tube is sheathed on the mouthpiece;

the elastic electrode and the second insulation ring are disposed in the copper ring; the third magnet is disposed on the copper ring; the copper ring is disposed on the cartridge; and the pneumatic switch is disposed on the control plate; the control plate is attached to the battery; the second silica gel is sheathed on the pneumatic switch; the control plate is disposed on the base; the battery, the control plate and the base are disposed in the cartridge; and the bottom cap is attached to one end of the cartridge to limit the base in the cartridge.

\* \* \* \* \*